United States Patent
Zorn et al.

(10) Patent No.: US 10,463,239 B2
(45) Date of Patent: Nov. 5, 2019

(54) MOTORISED AND MODULAR INSTRUMENTATION DEVICE AND ENDOSCOPY SYSTEM COMPRISING SUCH A DEVICE

(71) Applicants: UNIVERSITE DE STRASBOURG (ETABLISSMENT PUBLIC NATIONAL A CARACTERE SCIENTIFIQUE, CULTUREL ET PROFESSIONNEL), Strasbourg (FR); CENTRE NATIONAL DE LA RECHERCHE SCIENTIFIQUE (ETABLISSMENT PUBLIC NATIONAL A CARACTERE SCIENTIFIQUE ET TECHNOLOGIQUE), Paris (FR)

(72) Inventors: Lucile Zorn, Colmar (FR); Philippe Zanne, Roppenheim (FR); Florent Nageotte, Wettolsheim (FR); Michel De Mathelin, Strasbourg (FR)

(73) Assignees: UNIVERSITE DE STRASBOURG (ETABLISSMENT PUBLIC NATIONAL A CARACTERE SCIENTIFIQUE, CULTUREL ET PROFESSIONNEL, Strasbourg (FR); CENTRE NATIONAL DE LA RECHERCHE SCIENTIFIQUE (ETABLISSMENT PUBLIC NATIONAL A CARACTERE SCIENTIFIQUE ET TECHNOLOGIQUE), Paris (FR)

( * ) Notice: Subject to any disclaimer, the term of this patent is extended or adjusted under 35 U.S.C. 154(b) by 788 days.

(21) Appl. No.: 14/382,915

(22) PCT Filed: Mar. 8, 2013

(86) PCT No.: PCT/FR2013/050487
§ 371 (c)(1),
(2) Date: Sep. 4, 2014

(87) PCT Pub. No.: WO2013/132194
PCT Pub. Date: Sep. 12, 2013

(65) Prior Publication Data
US 2014/0378761 A1    Dec. 25, 2014

(30) Foreign Application Priority Data

Mar. 8, 2012 (FR) .................................... 12 52109

(51) Int. Cl.
*A61B 1/018* (2006.01)
*A61B 1/00* (2006.01)
(Continued)

(52) U.S. Cl.
CPC ............ *A61B 1/018* (2013.01); *A61B 1/0016* (2013.01); *A61B 1/0052* (2013.01);
(Continued)

(58) Field of Classification Search
CPC ......... A61B 34/30; A61B 34/32; A61B 34/35; A61B 34/37; A61B 34/70–72;
(Continued)

(56) References Cited

U.S. PATENT DOCUMENTS

| 5,558,619 A | 9/1996 | Kami et al. |
| 2005/0119522 A1 | 6/2005 | Okada |

(Continued)

FOREIGN PATENT DOCUMENTS

| DE | 25 04 663 A1 | 8/1976 |
| DE | 3 928 532 A1 | 3/1991 |

(Continued)

OTHER PUBLICATIONS

International Search Report, dated Jul. 17, 2013, from corresponding PCT application.

*Primary Examiner* — Ryan N Henderson
(74) *Attorney, Agent, or Firm* — Young & Thompson

(57) ABSTRACT

A motorized, modular instrumentation device and an endoscopy system including such device. The motorized, modular instrumentation device includes at least one operational unit mounted on at least one support structure and integrating a motorized medical instrument module including, first, an elongated medical instrument with a tool arranged on one distal end, it being possible to bend the corresponding end portion of the instrument, and second, at least one electrical actuating element controlling the operation of the tool and/or (Continued)

the bending of the distal end portion, via transmission elements extending within the elongated body of the instrument. The actuating element(s) is/are installed in a hollow body connected to the proximal end of the instrument and the hollow body is itself arranged, with rotational guiding, within a reception housing adapted to move, at least translationally, on the support structure, the movements of the hollow body and the reception housing being motorized.

19 Claims, 17 Drawing Sheets

(51) Int. Cl.
| | |
|---|---|
| A61B 1/005 | (2006.01) |
| A61B 34/00 | (2016.01) |
| A61B 17/00 | (2006.01) |
| A61B 17/29 | (2006.01) |
| A61B 90/50 | (2016.01) |
| A61B 34/30 | (2016.01) |

(52) U.S. Cl.
CPC ........ *A61B 1/0057* (2013.01); *A61B 1/00133* (2013.01); *A61B 1/00149* (2013.01); *A61B 34/70* (2016.02); *A61B 34/30* (2016.02); *A61B 90/50* (2016.02); *A61B 2017/003* (2013.01); *A61B 2017/00398* (2013.01); *A61B 2017/2905* (2013.01)

(58) Field of Classification Search
CPC ...... A61B 34/74; A61B 2034/301–306; A61B 1/00087; A61B 1/00131; A61B 1/00133; A61B 1/00147; A61B 1/00149; A61B 1/00154; A61B 1/0016; A61B 1/01; A61B 1/005; A61B 1/0051; A61B 1/0052; A61B 1/0053; A61B 1/0055; A61B 1/0056; A61B 1/0057; A61B 1/0058; A61B 1/008; A61B 1/018
USPC ................ 600/102, 104, 106, 107, 114, 115, 600/121–125, 139–152, 417, 427, 429; 606/1, 108, 130; 700/245

See application file for complete search history.

(56) References Cited

U.S. PATENT DOCUMENTS

| | | |
|---|---|---|
| 2006/0270904 A1 | 11/2006 | Kupferschmid et al. |
| 2007/0043338 A1* | 2/2007 | Moll ...................... A61B 34/77 606/1 |
| 2008/0046122 A1 | 2/2008 | Manzo et al. |
| 2008/0103358 A1 | 5/2008 | Suzuki |
| 2010/0274078 A1 | 10/2010 | Kim et al. |
| 2011/0130718 A1* | 6/2011 | Kidd ................. A61M 25/0105 604/95.01 |
| 2011/0237881 A1* | 9/2011 | Kunz ................. A61B 1/00147 600/106 |
| 2013/0035548 A1* | 2/2013 | Ianchulev .......... A61B 1/00052 600/120 |
| 2013/0060278 A1* | 3/2013 | Bozung ............ A61B 17/32002 606/205 |
| 2013/0096574 A1* | 4/2013 | Kang ................. A61B 17/1622 606/130 |
| 2014/0166023 A1* | 6/2014 | Kishi ...................... A61B 17/29 128/849 |

FOREIGN PATENT DOCUMENTS

| | | |
|---|---|---|
| DE | 4 213 418 A1 | 10/1992 |
| DE | 1 99 189 61 A1 | 11/2000 |
| EP | 0 078 017 A2 | 5/1983 |
| EP | 1 726 254 A1 | 11/2006 |
| EP | 1 980 213 A2 | 10/2008 |
| EP | 1 987 789 A1 | 11/2008 |

* cited by examiner

MOTORISED AND MODULAR INSTRUMENTATION DEVICE AND ENDOSCOPY SYSTEM COMPRISING SUCH A DEVICE

This invention relates to the field of endoscopes, particularly flexible endoscopes, in particular in relation to endoluminal and transluminal surgery, and it has as its objects a motorized and modular instrumentation device for an endoscope or a device that is analogous to the rigid or flexible elongated guide and a flexible medical endoscopic system comprising at least one such device.

Numerous endoscope embodiments or the like, flexible or not, are already known in the state of the art, for example by the documents DE3928532, DE19918961, EP1726254 and DE2504663.

Such devices generally comprise an elongated body designed to be introduced into the body of the patient and comprising one or more functional channels for the passage of fluids or the installation of medical or optical instruments, with an elongated and generally flexible structure, whose ends that are equipped with tools, actuators or the like emerge from the distal end of the elongated body of the endoscope (located in the patient at the intervention zone or area of interest).

The proximal end of the elongated body of the endoscope, which remains outside of the patient, is connected mechanically and functionally to a control grip or control unit that makes it possible to move the elongated body in translation and in rotation and to inflect or to curve the distal end of said body.

In addition, said grip is equipped with passages for the introduction of instruments into the corresponding channels of the elongated body, each of these instruments comprising its own control means (for example, in the form of secondary or auxiliary grips) making possible the actuation of the tool, the bending of the distal end of the instrument, and the movement in translation and/or in rotation of said instrument in its channel by the operator.

So as to limit the forces to be provided by the latter and to make the use of the endoscope easier, more reliable, and simpler, in particular during precise and prolonged interventions, it was proposed to motorize at least some of the maneuvers, in particular those linked to the bending of the ends of the instruments and to the actuation of the tools.

Such prior motorized embodiments are known in particular by the documents DE 2504663, EP0078017, DE4213418, as well as by the following publications:

"Design of a Telemanipulated System for Transluminal Surgery" (Conception d'un système télémanipulépour la chirurgie transluminale), B. Bardou et al.: IEEE Engineering in Medicine and Biology Conference (EMBC 2009), Minneapolis, Minn., U.S., September 2009;

"Control of a Multiple Sections Flexible Endoscopic System" (Contrôle d'un système endoscopique flexible à sections multiples), B. Bardou et al.: International Conference on Intelligent Robots and Systems (IROS), Taipei, Taiwan, pp. 2345-2350, October 2010;

"Design of a Robotized Flexible Endoscope for Natural Orifice Transluminal Endoscopic Surgery" (Conception d'un endoscope flexible robotisé pour la chirurgie transluminale par orifice naturel), B. Bardou et al.: Computational Surgery and Dual Training," M. Garbey et al. (Eds.), Chapter 9, pp. 155-170, Springer, ISBN: 978-1-4419-1122-3, 2010.

However, there is currently a demand also for motorizing the movements of instruments, and even the movement of the endoscope itself, in particular for making possible a remote control, without direct physical action of the operator, of the instruments and, if necessary, of the endoscope, after their initial installation.

In addition, it would be advantageous that the instruments also have a compact structure at their parts remaining on the outside, integrate moving parts isolated from the outside environment, and are able to be easily interchanged and that the same endoscopic system can accommodate instruments of different types, with the possibility of motorized actuation and movement.

This invention has as its object to provide a solution that meets at least the primary needs disclosed above.

For this purpose, the invention has as its object a motorized and modular instrumentation device for an endoscope or the like, in particular a flexible endoscope, comprising at least one operational unit mounted on at least one support structure, preferably an articulated support structure, with the unit or each unit integrating a motorized medical instrument module comprising, on the one hand, an elongated medical instrument with an actuator or a tool placed at a distal end, with the corresponding end portion of the instrument being able to undergo bending or arching in at least one plane and/or in at least one direction and, on the other hand, at least one motorized actuating means controlling the operating of the tool or the actuator and/or the bending or the arching of the distal end portion, where this is done by means of transmission means extending into the elongated body of the medical instrument, the latter also being able to be subjected to movements in translation in the direction of its longitudinal axis and to movements in rotation around this axis.

This instrumentation device is characterized in that the actuating means is (are) mounted in a hollow body connected to the proximal end of the medical instrument and in that said hollow body is itself placed, with guiding in rotation around a suitable median axis extending the longitudinal axis of the medical instrument, in a receiving housing, where the latter is mounted with the ability to move at least in translation in the direction of the median axis of the hollow body, on the support structure, with the movements of the hollow body and of the receiving housing being motorized.

The invention also has as its object a flexible endoscopic system comprising, on the one hand, an elongated body with at least one, preferably at least two, longitudinal functional channel(s) each intended to accommodate a medical instrument whose distal end that carries the actuator or the tool can emerge from the distal end of said elongated body, and, on the other hand, a control unit or control grip connected to the proximal end of the elongated body and comprising, for the medical instrument or for each medical instrument, an introduction opening that extends through a corresponding longitudinal channel, with said unit or grip integrating actuating means controlling the bending or the arching of the distal end portion at least of the elongated body.

This endoscopic system is characterized in that it comprises in addition at least one motorized and modular instrumentation device as mentioned above, whose medical instrument is placed in the functional channel or a functional channel with the ability to move in translation and in rotation.

The invention will be better understood owing to the description below, which relates to preferred embodiments, provided by way of examples that are non-limiting and explained with reference to the accompanying diagrammatic drawings, in which.

Figure 1A:
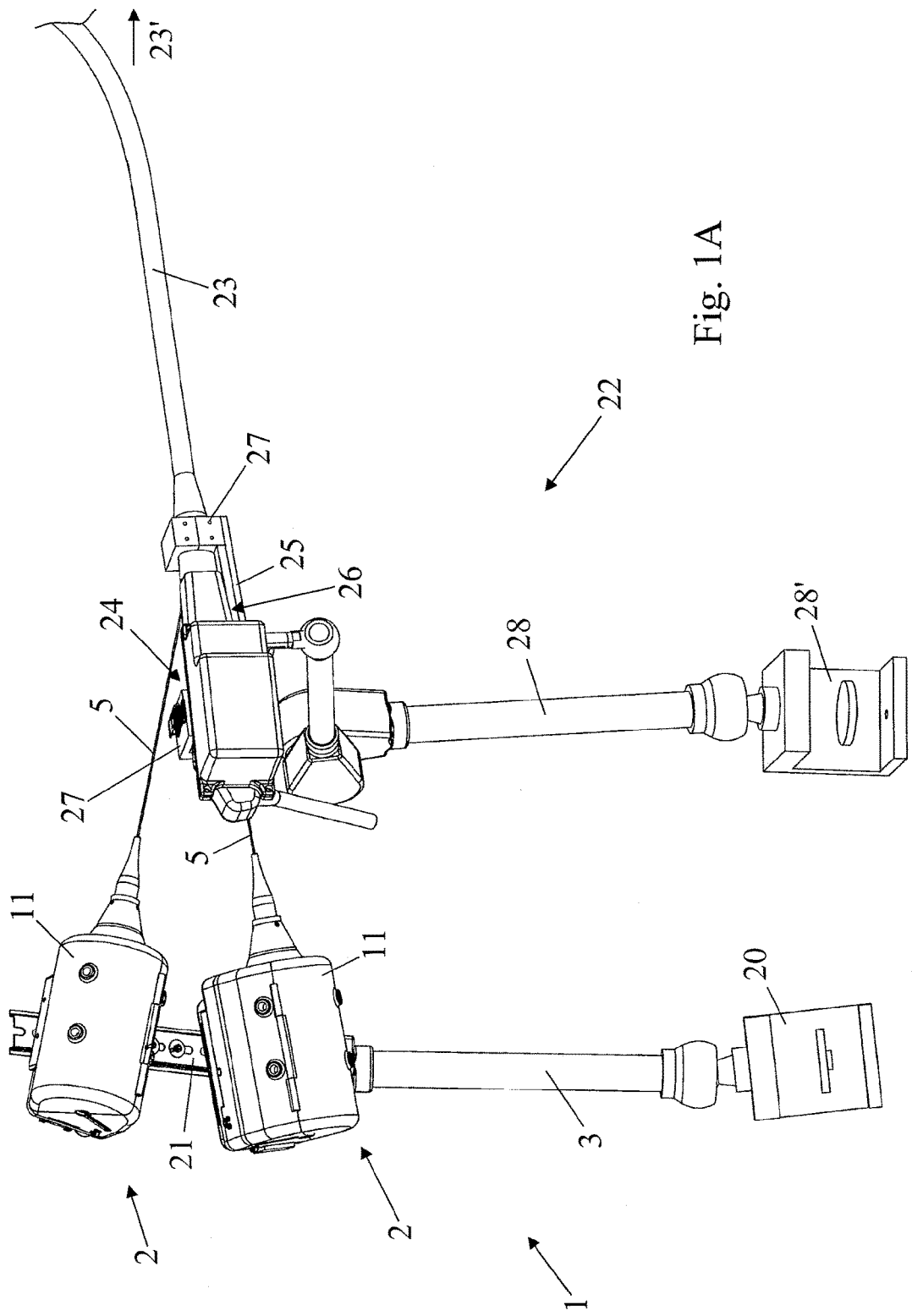
FIGS. 1A and 1B are perspective views, in two essentially opposite directions, of a flexible endoscopic system according to a first embodiment of the invention comprising an instrumentation device according to the invention and two separate support structures.
Figure 1B:
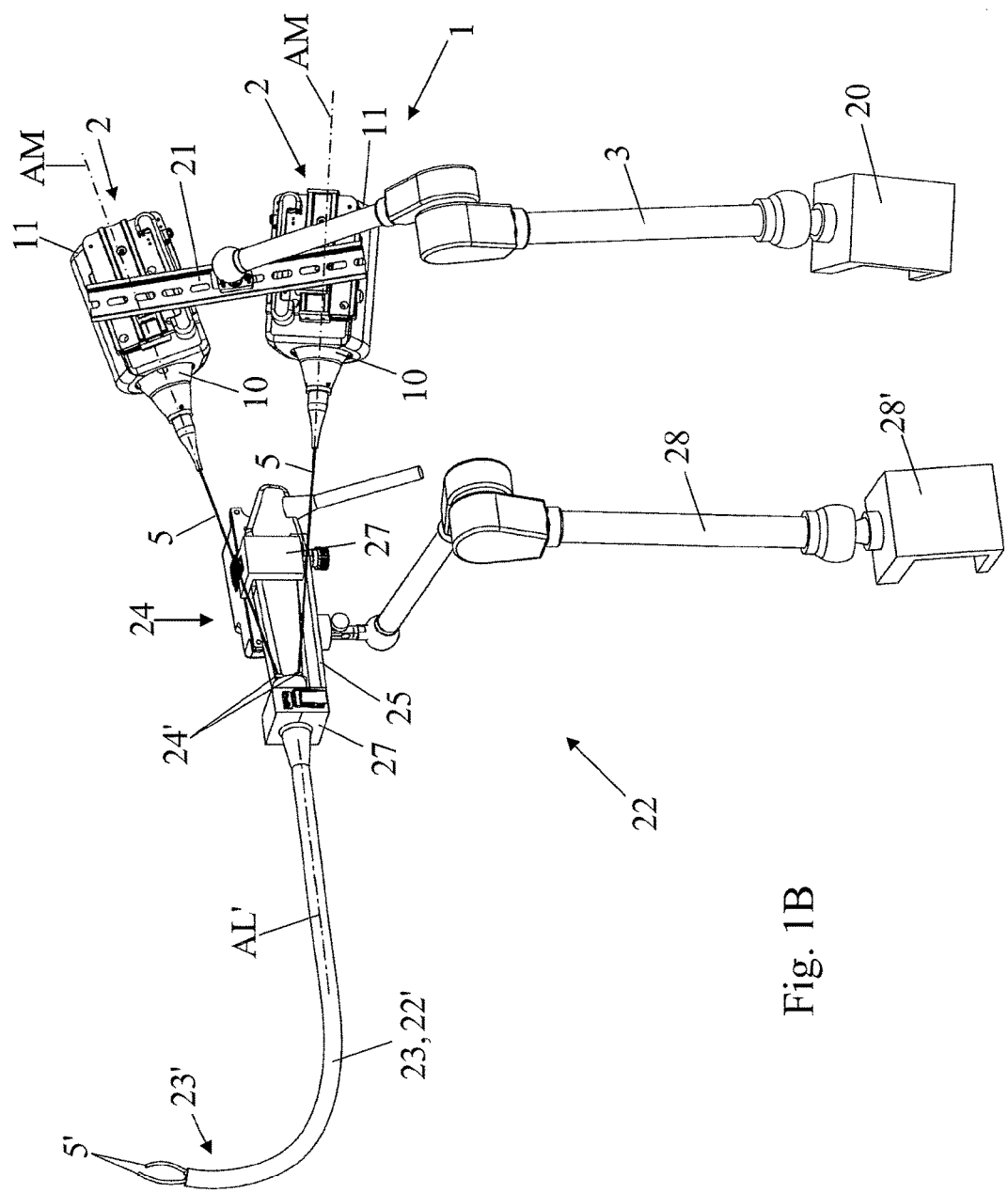
Figure 2:
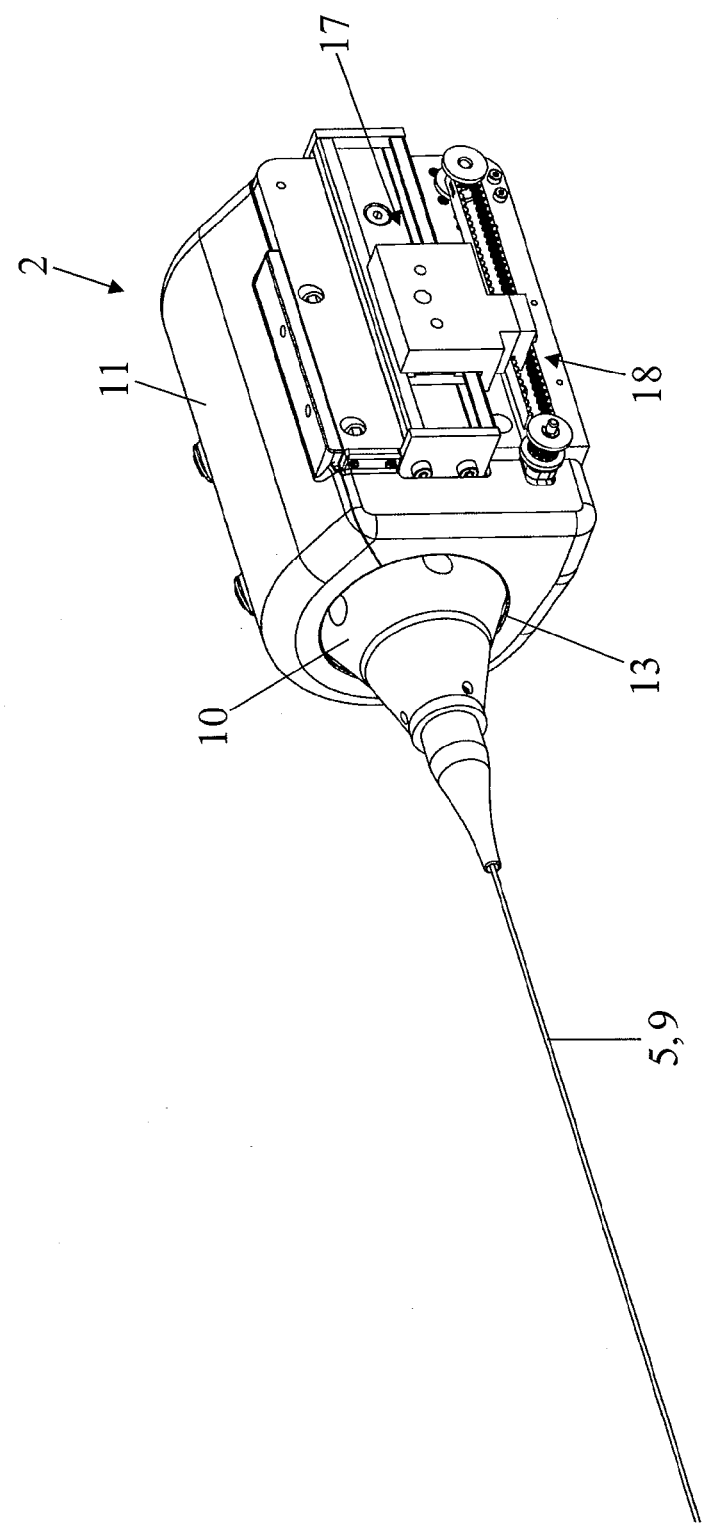
FIG. 2 is a perspective view of an operational unit that is part of the device shown in FIGS. 1A and 1B.
Figure 11A:
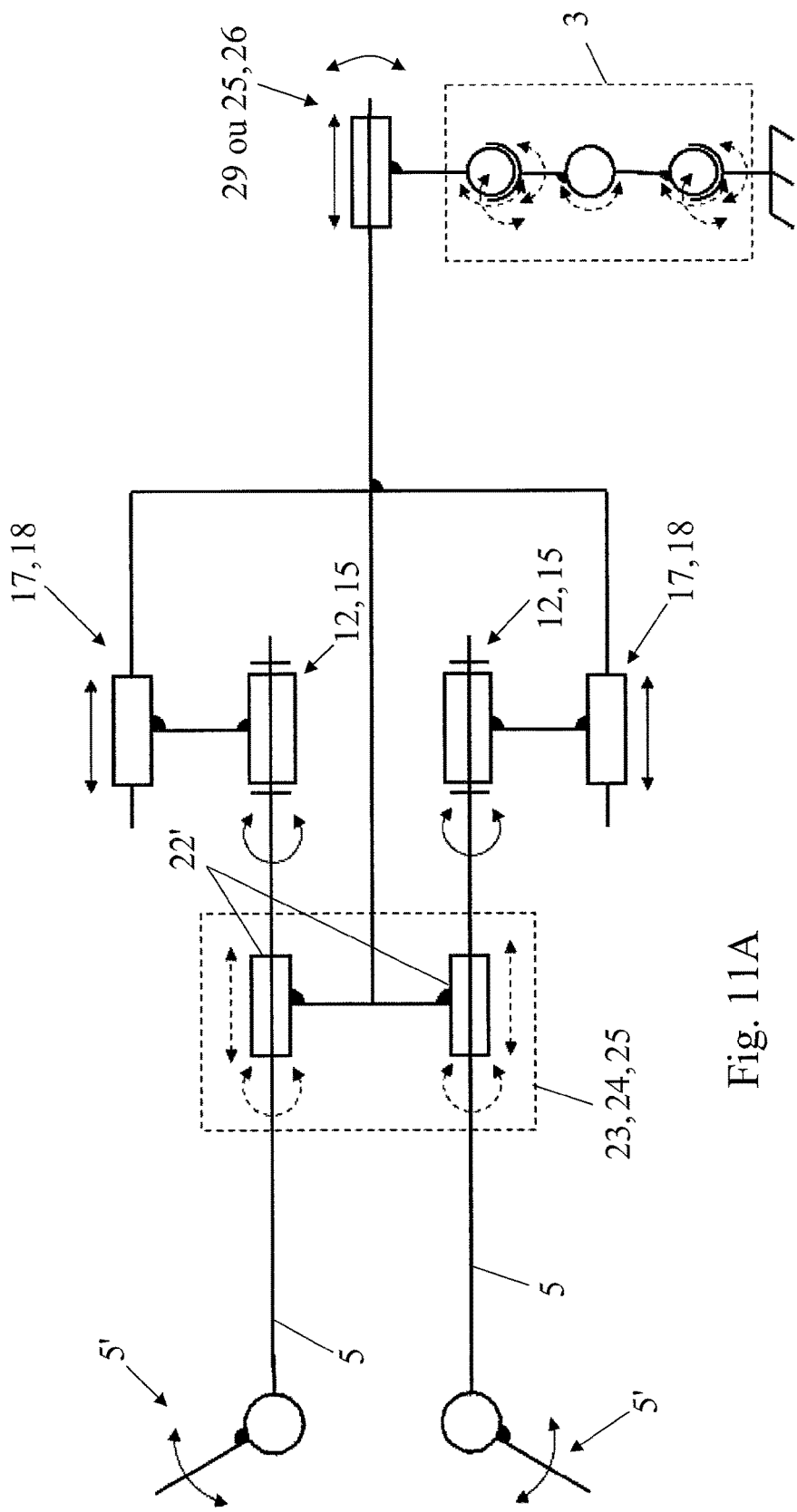
FIGS. 11A and 11B are mechanical kinematic diagrams of two variants of another embodiment of an endoscopic system as shown in FIGS. 1A and 1B.
Figure 11B:
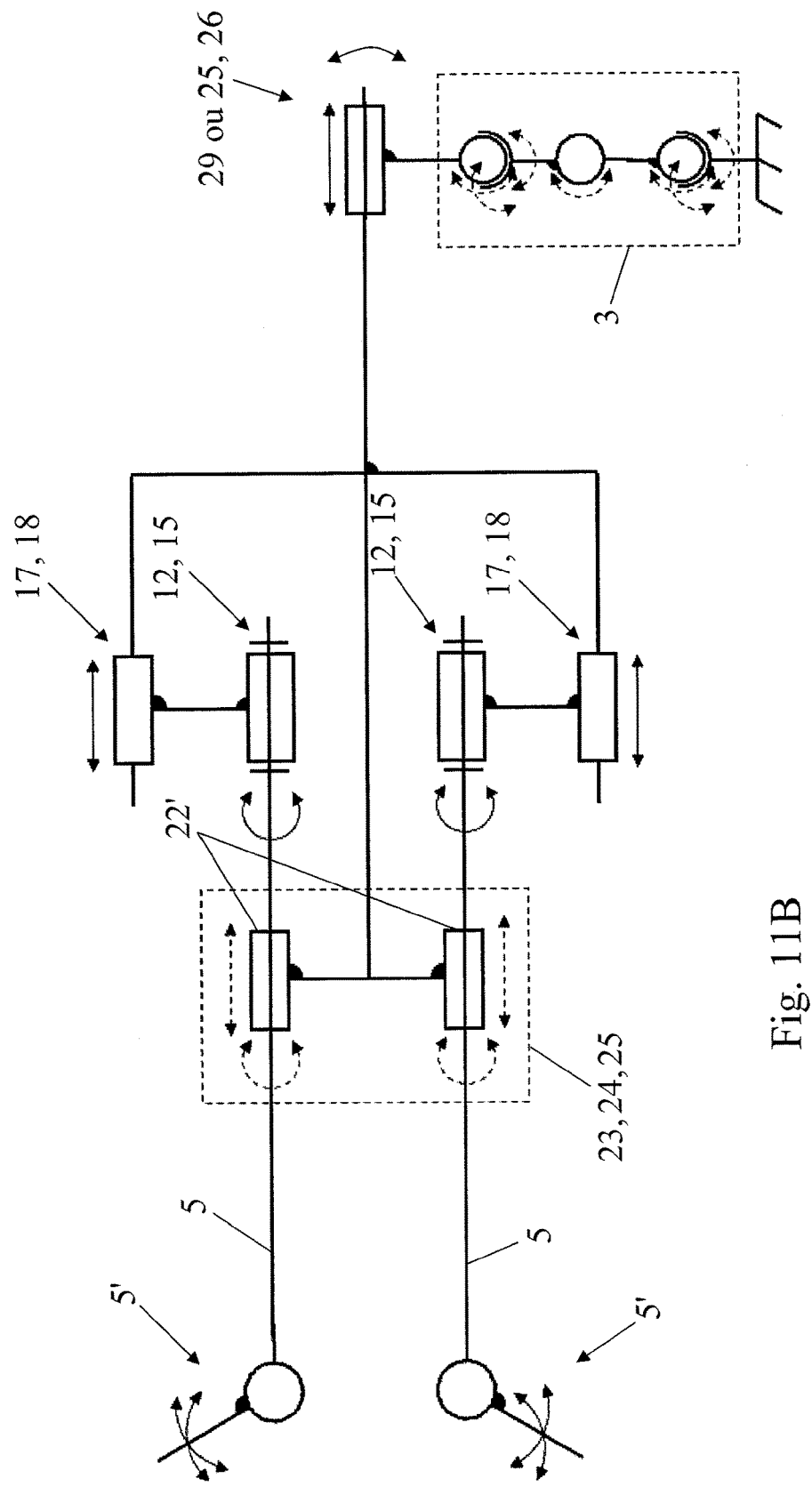
Figure 12:
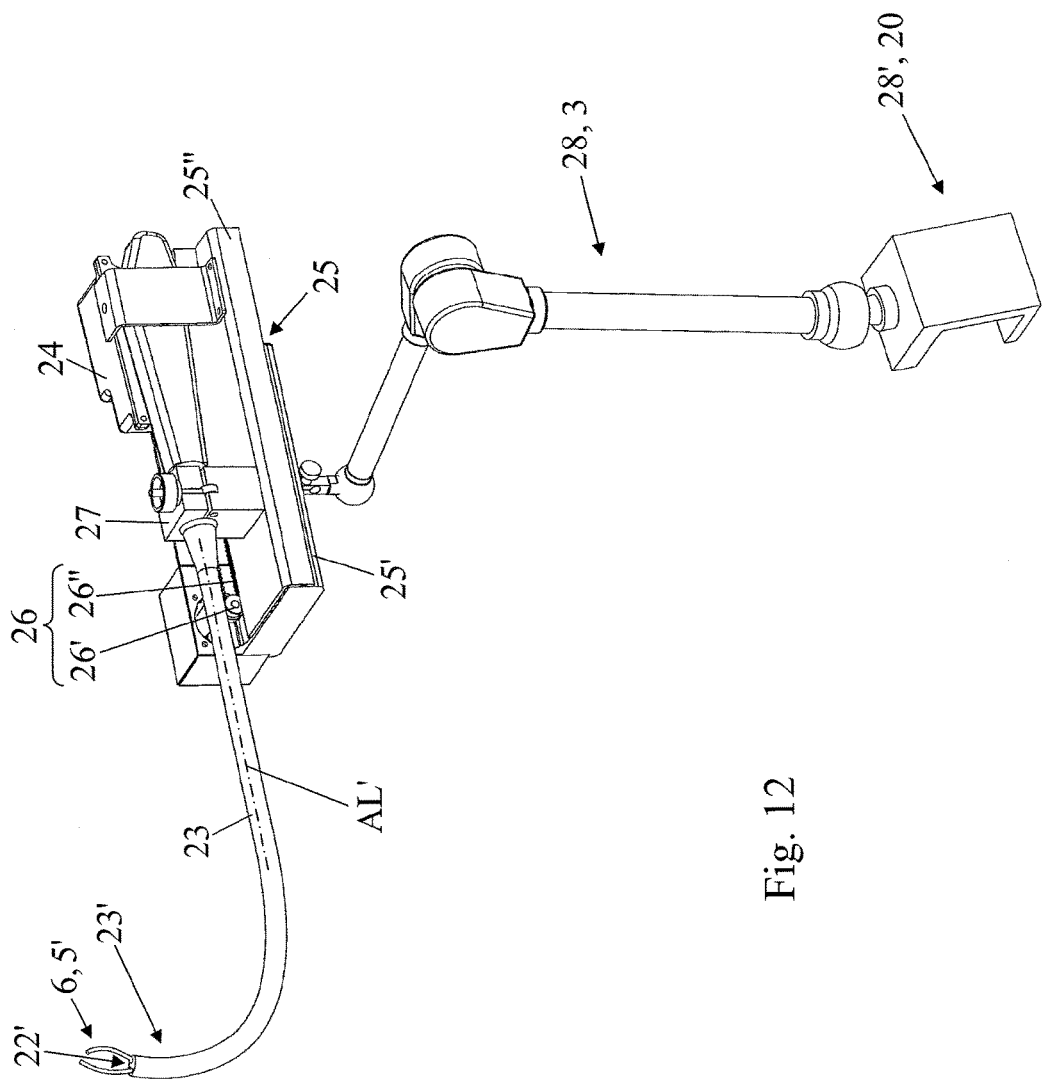
Figure 13:
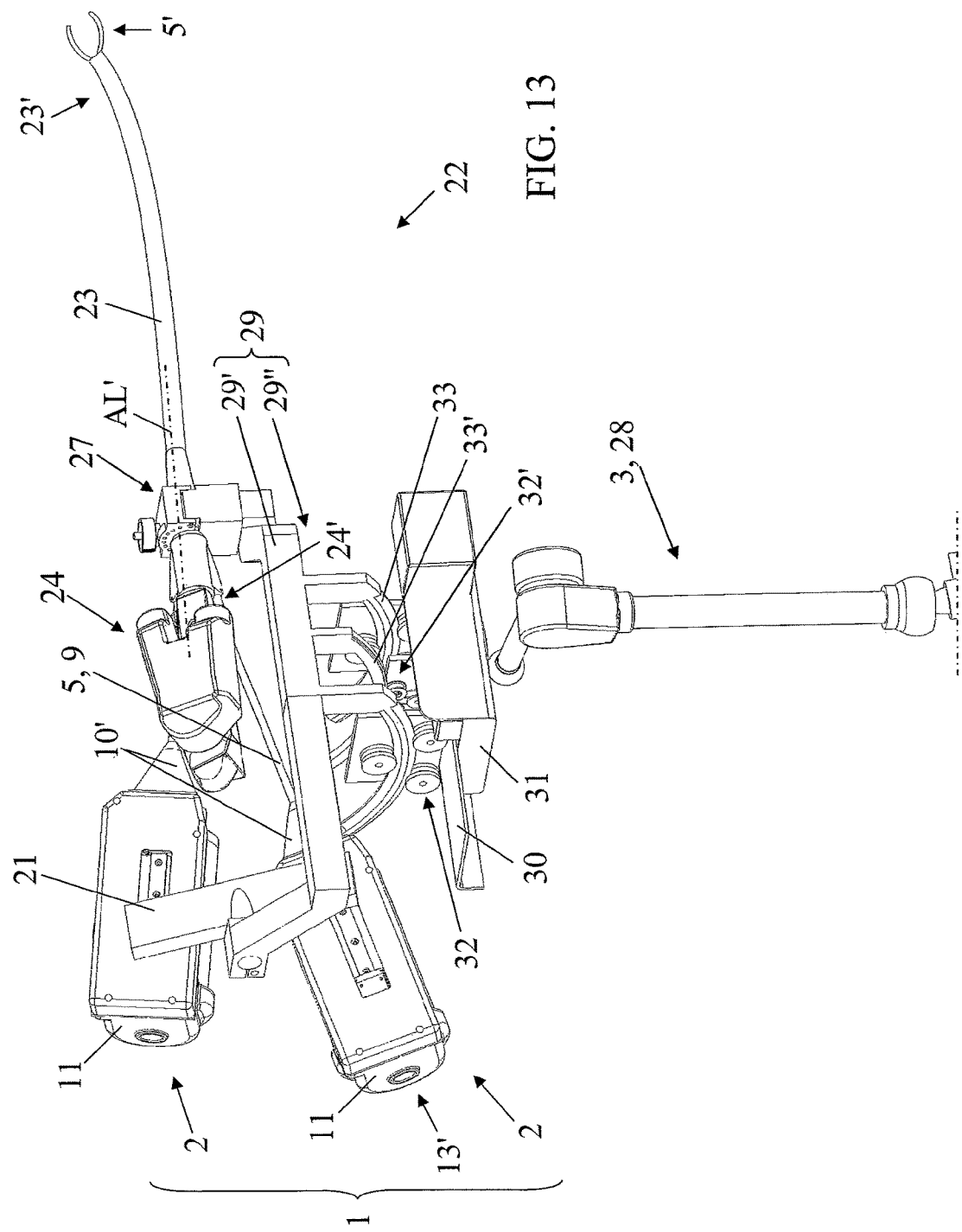

FIG. 12 is a perspective view, similar to that of FIG. 1B, partially showing a flexible endoscopic system (the modules of instruments are not shown), in accordance with another variant embodiment of the mounting of the control grip, and FIG. 13 is a perspective view, similar to that of FIG. 1B, of a flexible endoscopic system according to another embodiment of the invention, comprising an instrumentation device according to the invention and corresponding to the kinematic diagrams of FIGS. 11A and 11B, with a unique support structure.

FIGS. 1 to 8 illustrate, only partially for some, a motorized and modular instrumentation device 1 for an endoscope or the like, in particular a flexible endoscope, with or without a viewing means.

This device 1 comprises at least one operational unit 2 mounted on at least one support structure 3, preferably articulated. The unit 2 or each unit 2 integrates a motorized medical instrument module 4 that comprises, on the one hand, an elongated medical instrument 5 with an actuator or a tool 6 placed on a distal end, with the corresponding end portion 5' of the instrument 5 being able to undergo bending or arching in at least one plane and/or in at least one direction and, on the other hand, at least one motorized actuating means 7, 7' controlling the operation of the tool or the actuator 6 and/or the bending or the arching of the distal end portion 5', by means of the transmission means 8, 8' extending into the elongated body 9 of the medical instrument, the latter also to be able to be subjected to movements in translation in the direction of its longitudinal axis AL and to movements in rotation around this axis.

In accordance with the invention, the actuating means 7, 7' is (are) mounted in a hollow body 10 connected to the proximal end 5" of the medical instrument 5, and said hollow body 10 is itself placed, with guiding in rotation around a suitable median axis AM extending the longitudinal axis AL of the medical instrument 5 into a receiving housing 11, with the latter being mounted with the ability to move, at least in translation, in the direction of the median axis AM of the hollow body 10, on the support structure 3, with the movements of the hollow body 10 and the receiving housing 11 being motorized.

Thus, the actuating means 7, 7' are combined in a closed chamber and separated from the outside environment, and the hollow body 10—with the medical instrument 5 that is connected to it—forms a structural and functional module 4 with a one-piece composition. In addition, the module or each module of the medical instrument 4 can, in its entirety, be moved in rotation and in translation relative to the support structure 3 that carries it, thus having at least the two degrees of freedom that the current medical instruments, equipped with suitable handling grips, have. However, owing to the invention, the possible movements according to these degrees of freedom are themselves also motorized.

As a result, the invention proposes in particular specific technical means that are suited to the targeted field of application, making it possible to provide improved maneuverability, an effective assistance to the operator, and faster manipulation of the instrumentation device, and therefore of the endoscopic system that it equips.

At present, "motorized" means actuating means 7, 7' whose initial driving force or initial driving does not have a human or manual origin but results from a transformation of energy into movement, optionally under the control of an operator.

Thus, the actuating means 7, 7' comprise or correspond to actuators such as, for example, motors or jacks that are electric, pneumatic or hydraulic (water-driven).

The following description more particularly has actuating means 7, 7' of the electric type, but actuating means that use another kind of energy can also be considered without exceeding the scope of the invention.

In a general manner in FIGS. 10 and 11 of the accompanying drawings, the arrows that symbolize the translational and rotational movements are indicated by continuous lines for the motorized movements/connections/articulations and by dotted lines for the passive connections/articulations.

In accordance with an advantageous embodiment of the invention, as shown more particularly in FIGS. 2 and 5 to 9, the hollow body 10, which advantageously delimits an essentially airtight chamber, has, at least on the outside, a structure for rotation around its median axis AM, advantageously circular cylindrical and preferably in the form of a shell with a tapered end 10' constituting a connecting interface with the body 9 of the medical instrument 5. In contrast, the receiving housing 11 comprises an arrangement of at least two spaced roller bearings 12 with a continuous or intermittent structure, ensuring the guiding in rotation of the hollow body 10 in the housing 11.

Figure 3:
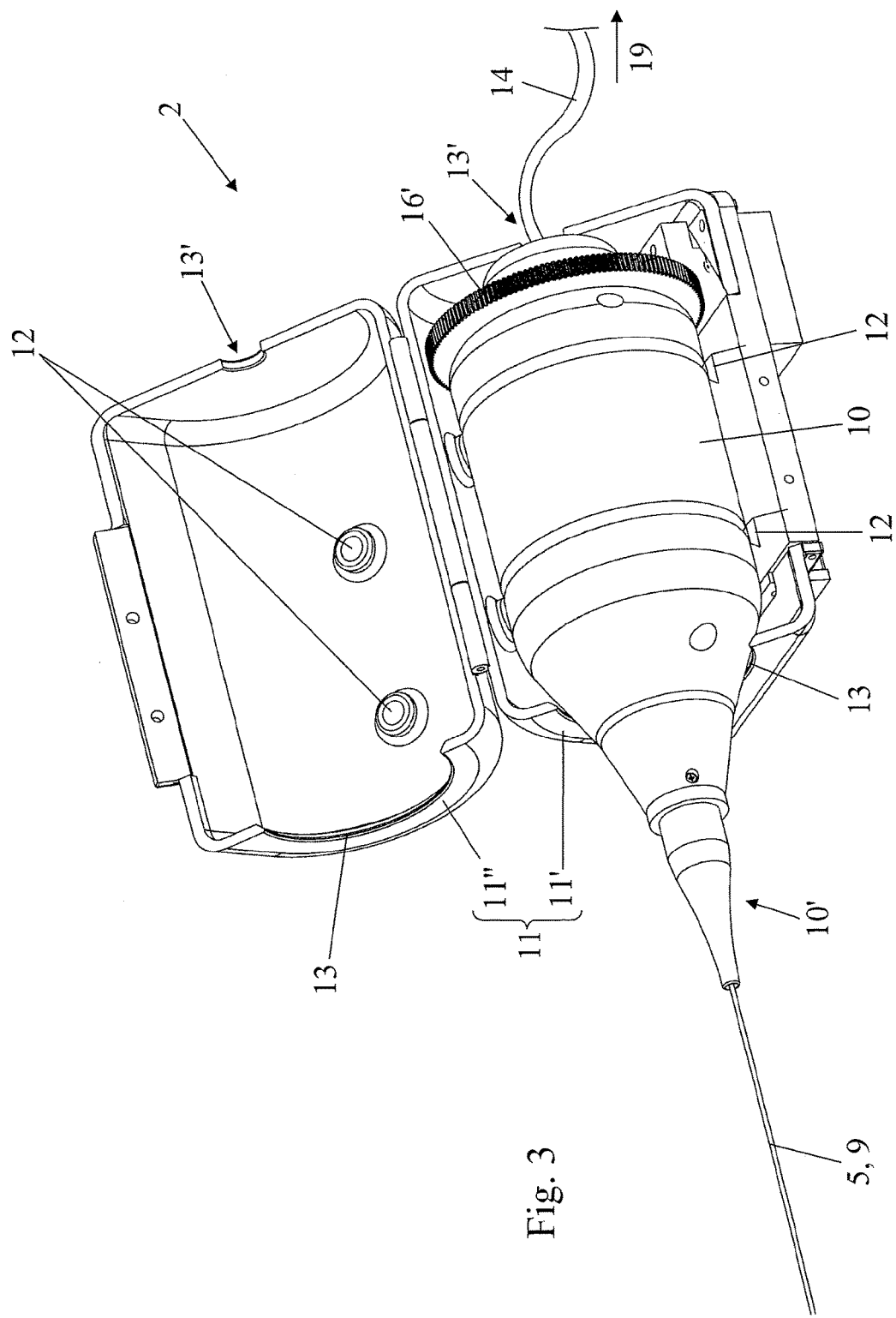
FIG. 3 is a perspective view on another scale and in another direction of the operational unit shown in FIG. 2, with the receiving housing being open.
Figure 4:
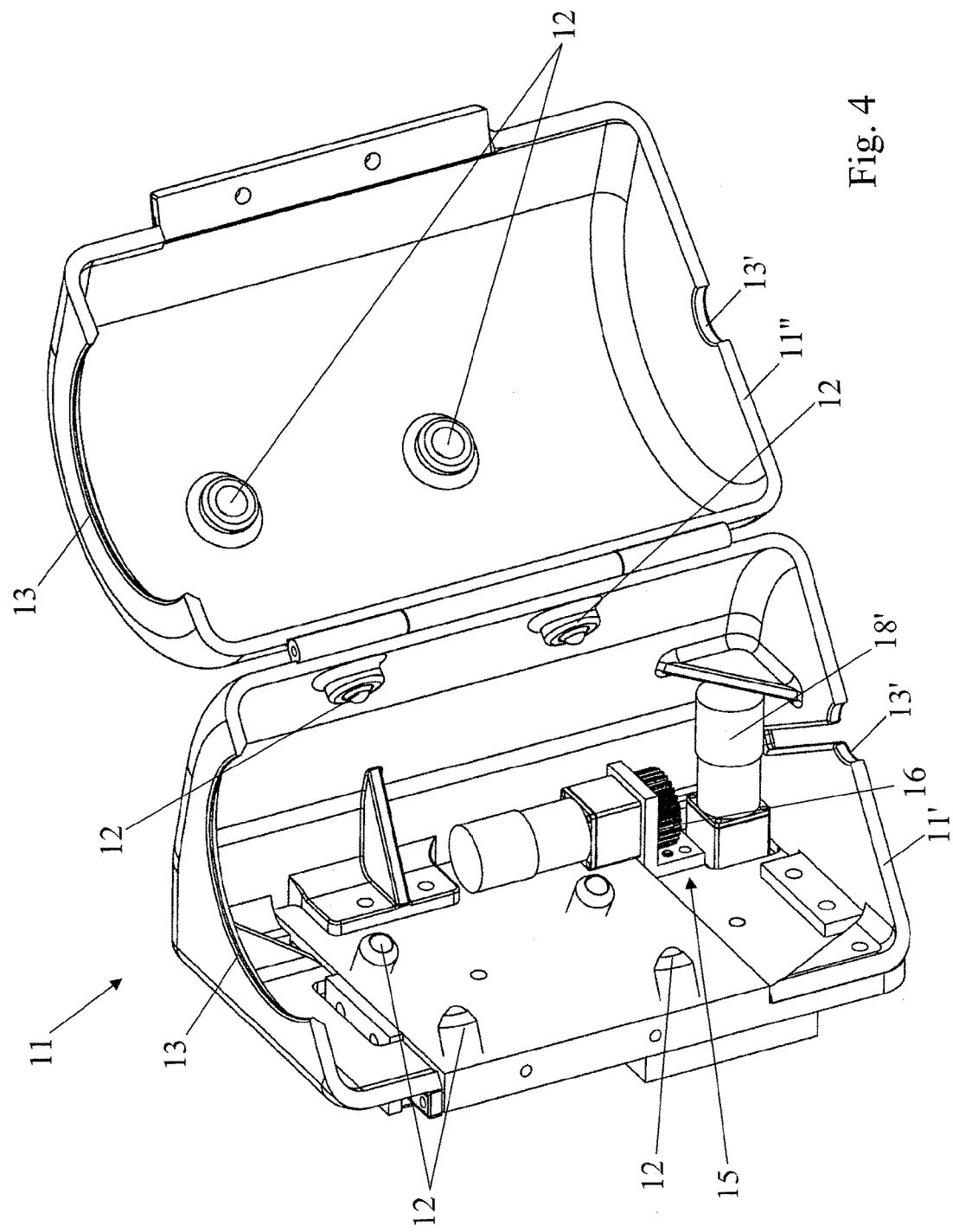
FIG. 4 is a perspective view of the receiving housing shown in FIG. 3, with the medical instrument module being removed.
Figure 5:
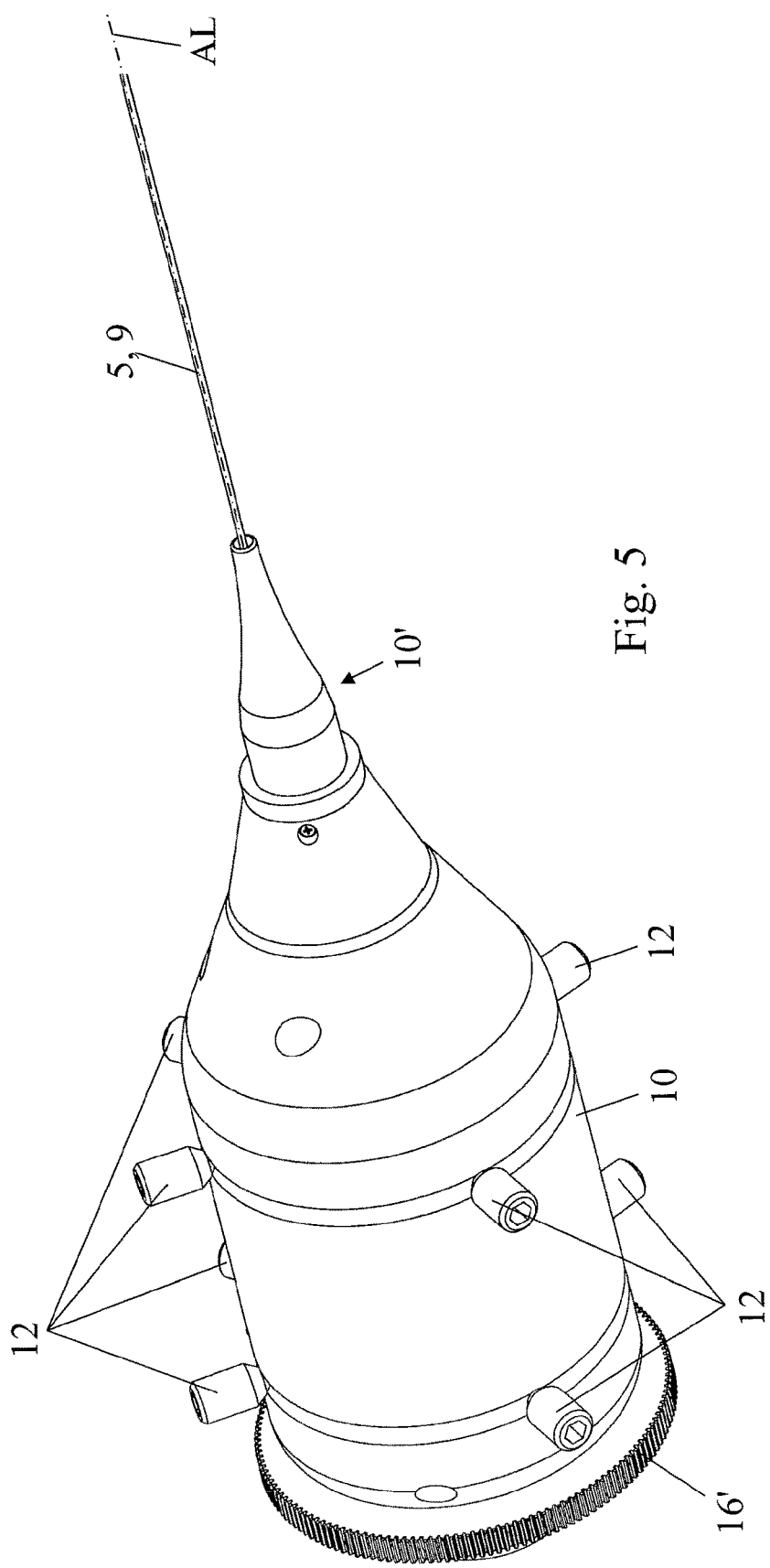
FIG. 5 is a perspective view of the instrument module shown in FIG. 3, with its means for guiding and driving in rotation.

As FIGS. 3 to 5 show, the bearings 12 can consist of ball screws integrated into the housing 11.

Of course, the hollow body 10 is preferably identical in terms of external shaping for the different types of instruments 5 in such a way as to be able to use the same receiving boxes 11, although the actuating means 7, 7' that each body 10 contains can be different.

The connection between the bodies 10 and 9 is rigid enough to allow a transmission of forces of traction/thrust and torque between them during their handling, preferably without breaking the sealing between them, and makes it possible to produce a one-piece instrument module 4.

The sealing of the hollow body 10 (for example formed by two half-shells, made of a material suitable for medical use, assembled in an airtight manner) makes it possible to insulate in a reliable manner the actuating means 7, 7' as well as the parts of the transmission means 8, 8' (for example of the cable or rod type or the like) that are external to the body 9 of the instrument 5 from the outside environment and to form a closed unit with said body 9.

As in particular FIGS. 3 and 4 show, the receiving housing 11 can consist of a shell made of at least two parts 11', 11", for example, two mutually articulated parts, one 11" of which forms a cover, allowing the introduction and the extraction of a hollow body 10 in an open position, with said shell comprising two opposing openings 13, 13' respectively intended, on the one hand, for the passage of the medical instrument 5 or a portion of the end 10' of the hollow body 10, and, on the other hand, for the passage of lines 14 for supply and/or control of the actuating means 7, 7' controlling the tool 6 and/or the flexible distal end 5'.

Figure 6:
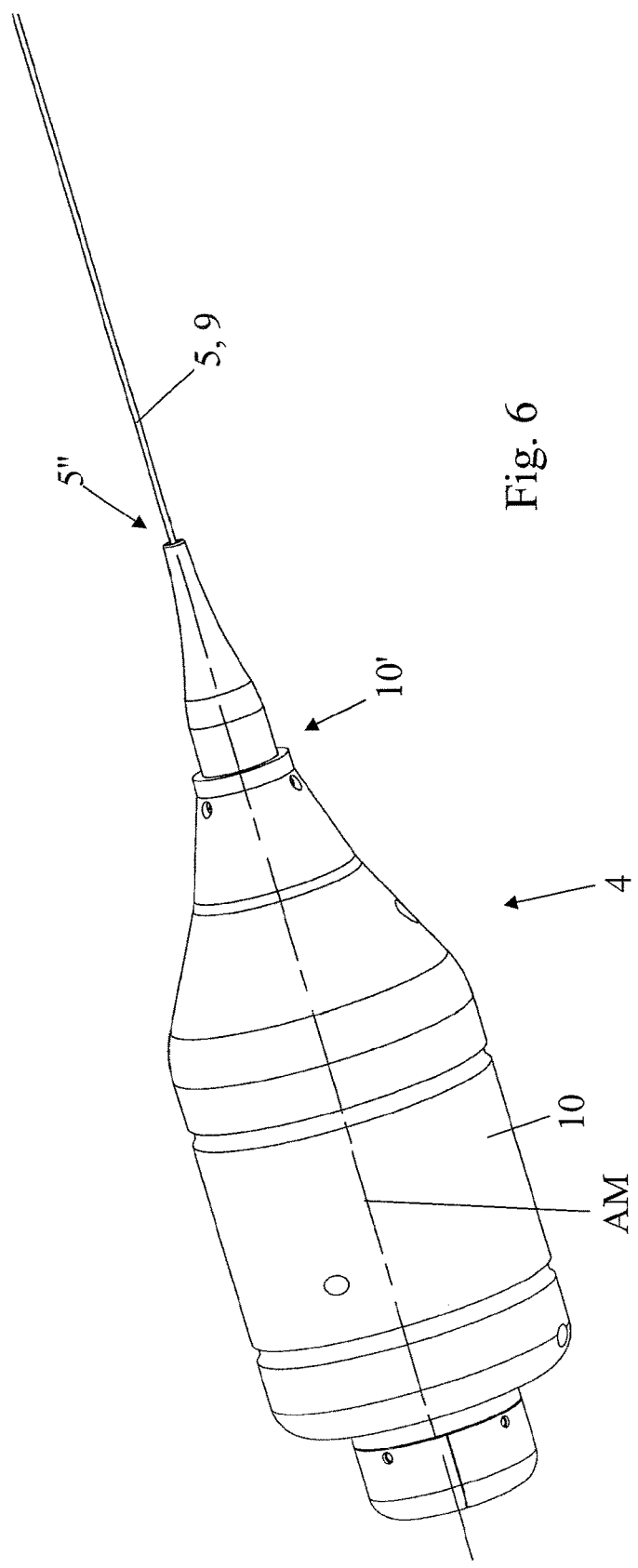
FIG. 6 is a depiction of an instrument module that is similar to that of FIG. 5, with the means for guiding and driving in rotation not being shown.
Figure 7:
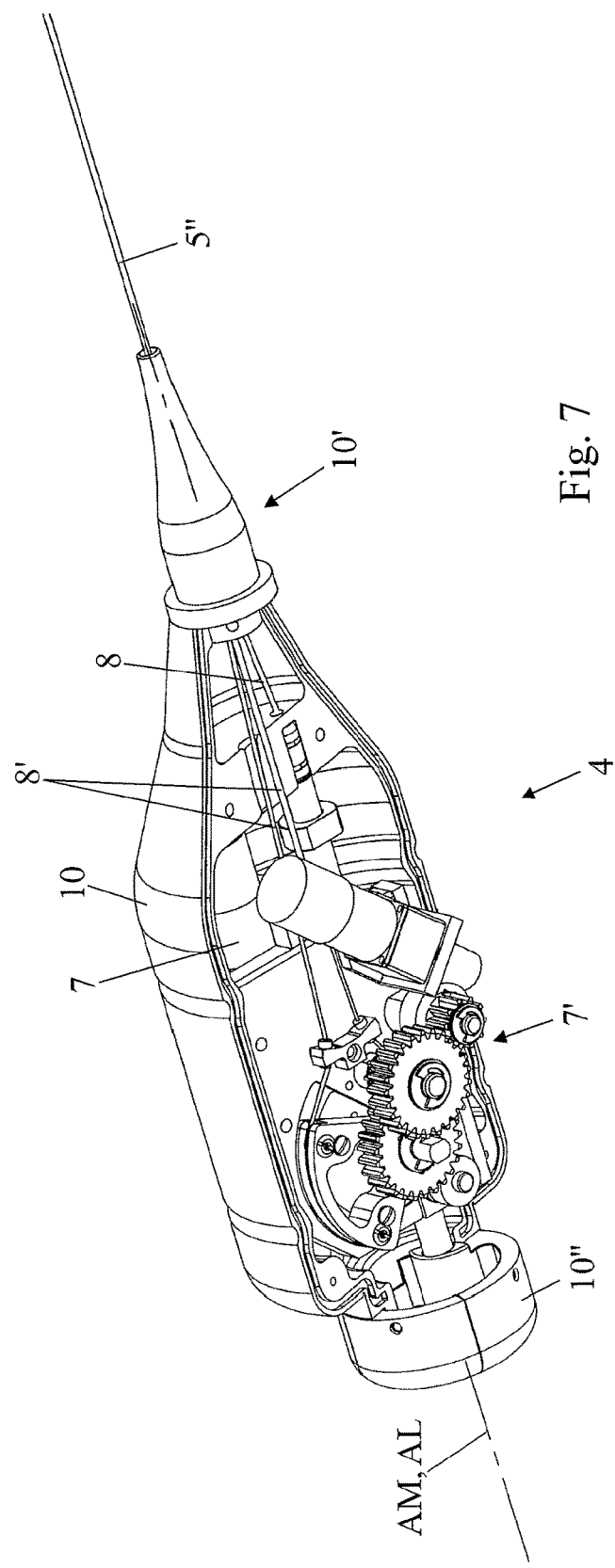
FIG. 7 is a perspective view of the instrument module shown in FIGS. 5 and 6, illustrating the actuating means controlling the bending of the end portion of the medical instrument, with a portion of the hollow body being removed.
Figure 8:
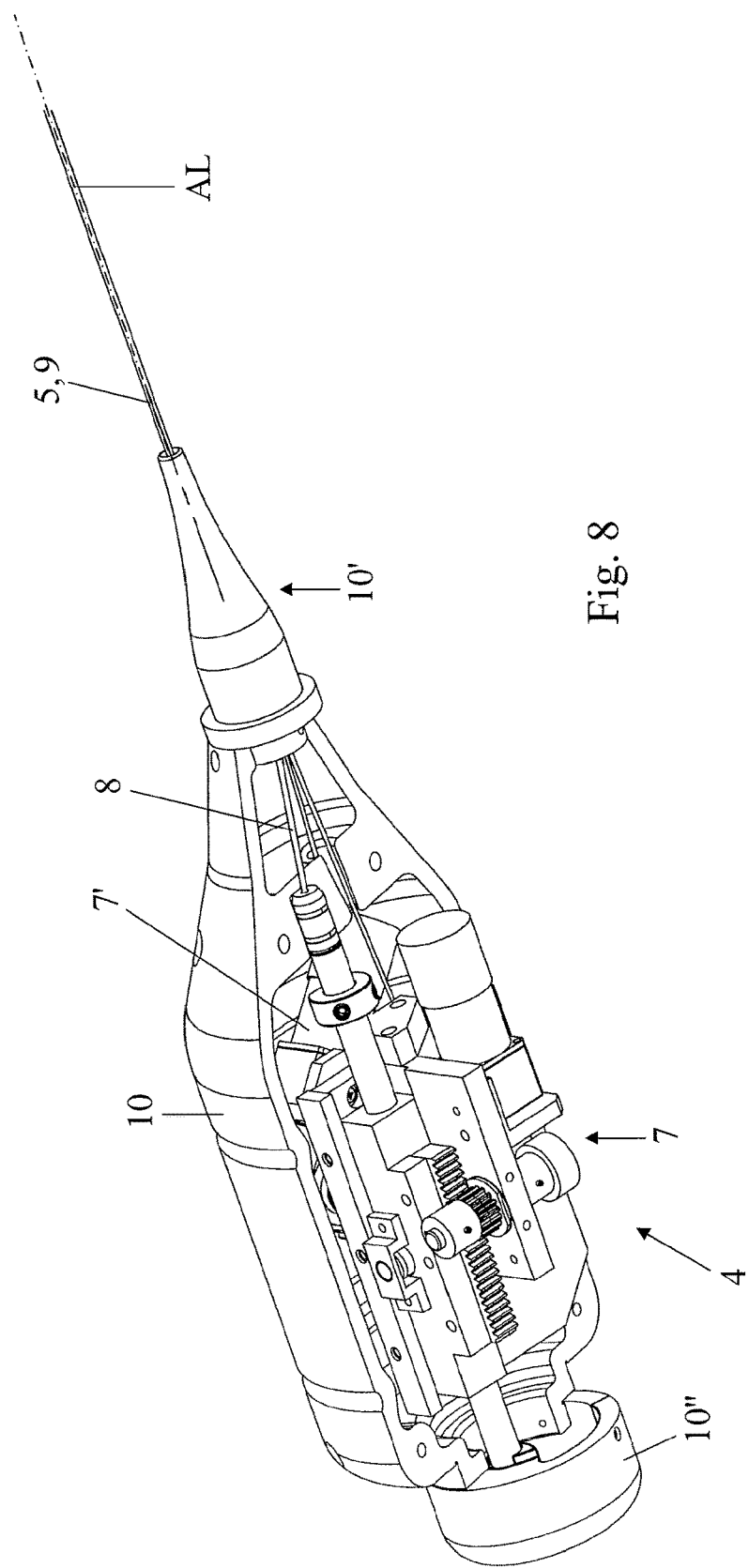
FIG. 8 is a perspective view that is similar to that of FIG. 7, illustrating the actuating means controlling the tool.

The lines 14 can, for example, pass through the chamber of the hollow body 10 at a connection or an airtight rotary passage interface 10" (FIGS. 6 to 8).

According to a characteristic of the invention, illustrated in FIGS. 3 to 5 of the accompanying drawings, the receiving housing 11 comprises a motorized mechanism 15 for controlled driving in rotation of the hollow body 10 around its median axis AM, for example formed by a motorized cogwheel 16 engaging with a ring gear 16' extending peripherally around said hollow body 10, with the connection between the latter and the medical instrument 5 being able to transmit this rotation to the elongated body 9 of said instrument 5.

Thus, all of the functional components participating in the controlled rotation of the hollow body 10, and therefore of the instrument 5, are housed inside the housing 11, which can optionally also form an airtight chamber by providing seals at the openings 13 and 13', compatible with the rotation of the hollow body 10 (O-ring seals with lips or the like).

In addition, by providing a ring gear 16' on the external periphery of the hollow body 10, it is possible to transmit to the latter significant torque for a power source of given power of the pinion 16, taking into account the large diameter ratio between said pinion and said wheel.

For the motorization of the translation of the instrument 5, it may be provided that the receiving housing 11 or each receiving housing 11 is mounted on the support structure 3 or a support structure 3 by means of a sliding connection 17, for example a slide connection, a carriage connection or a trolley connection, essentially in the direction of the longitudinal axis AL of the elongated medical instrument 5 that contains it, with the movement of the receiving housing 11 relative to the support structure 3 in question (according to AL) being controlled by a motorized driving mechanism 18, preferably integrated into said housing 11 (FIGS. 1B and 2), for example a mechanism with a rack or a toothed drive belt, whose motorized pinion is driven by an electric actuator 18' housed in the housing 11 (FIG. 4).

Of course, the external components of the sliding connection 17 and the drive mechanism can be covered by a protective hood (not shown).

By transferring the movement in translation of the instrument 5 at the level of the receiving housing 11, advantageously with a power source integrated inside the latter, it is possible to simplify the production of two power sources (decoupling between the movements in translation and in rotation), to reduce the space requirement of the hollow body 10, and to simplify the production of the mechanisms that it integrates.

As FIGS. 1A and 1B of the accompanying drawings show, the support structure 3 or each support structure 3 can consist of an articulated arm whose one end is equipped with an element 20 for attachment or rigid and removable assembly with a piece of equipment from an operating room, for example an operating table, and whose other end carries at least one, preferably two, receiving housing(s) 11, for example by means of a support crosspiece or an analogous part 21 allowing an oriented and optionally mutually spaced mounting when several receiving housings 11 are present.

Operationally, the arm 3 has a large number of degrees of freedom, preferably at least six, allowing a prepositioning (position and orientation) of the unit 2 or of each unit 2 relative to the operating table (not shown) and relative to the endoscope 22.

Physically, the arm 3 can have a variable number of articulations, optionally of different types (pivot, ball joint), optionally combined with telescopic portions, said articulations each able to be locked rigidly (in a removable manner) in a given position.

In addition, as already indicated, it can also comprise a removable attachment element 20 with another element of equipment from the installation site (for example, operating room).

Figure 9A:
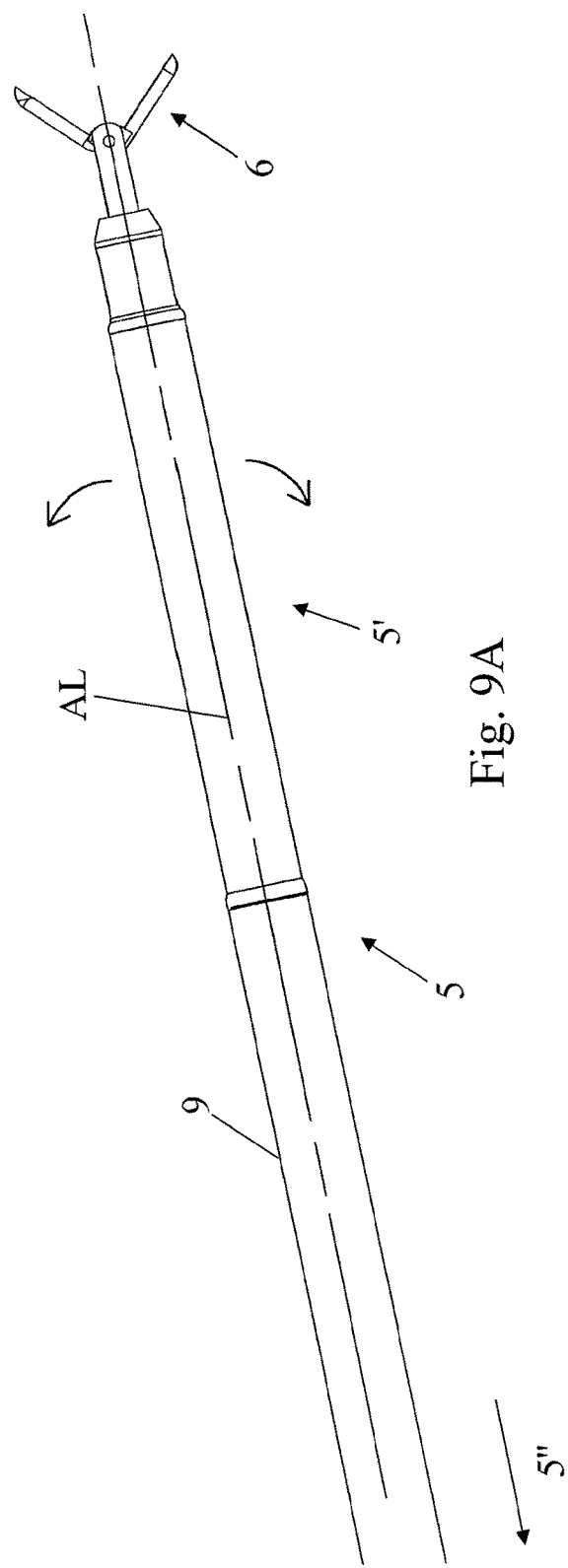
FIGS. 9A and 9B are partial views illustrating the end portion of a tool that is part of a medical instrument according to the invention, illustrating the bending possibilities in a plane.
Figure 9B:
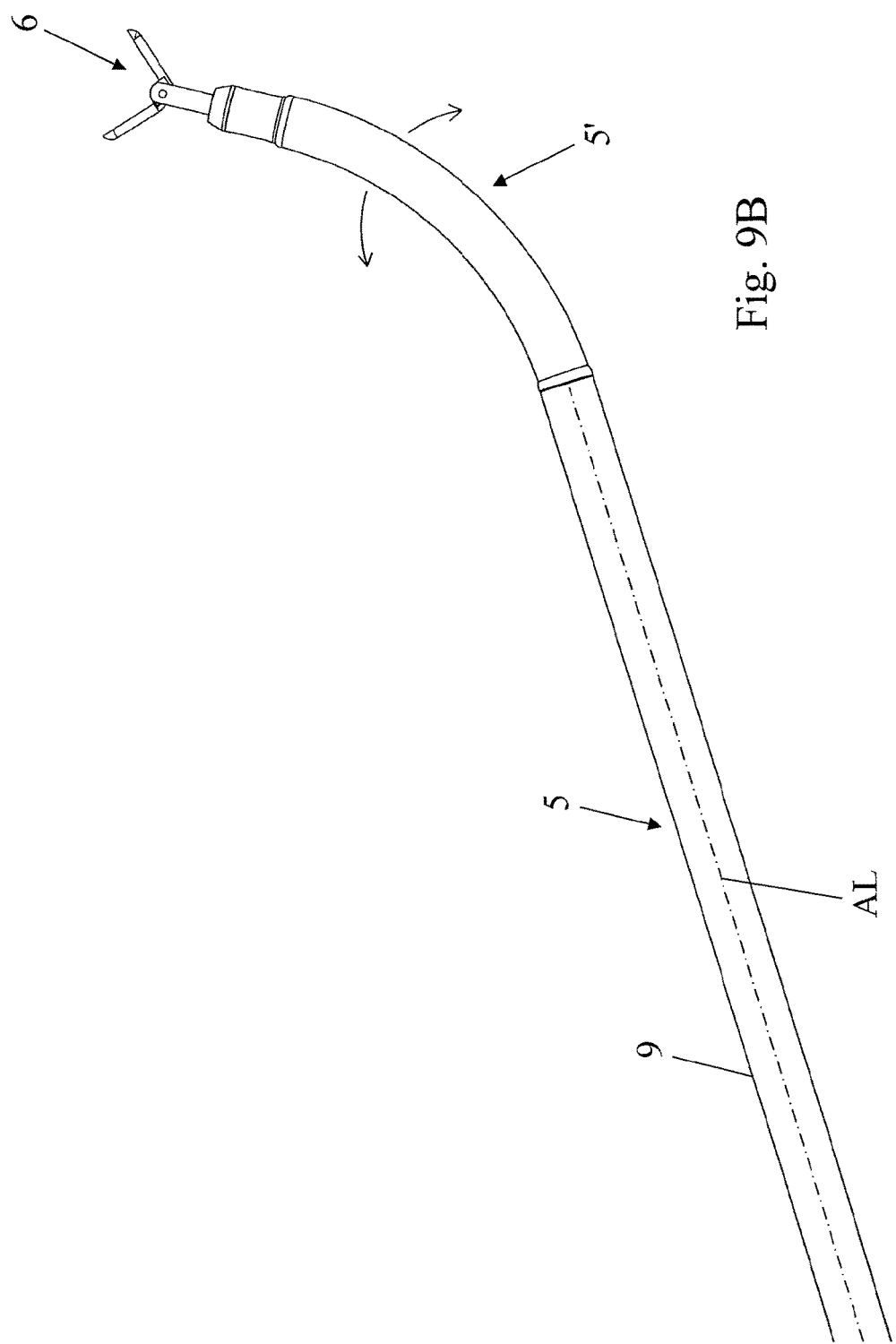
Figure 10A:
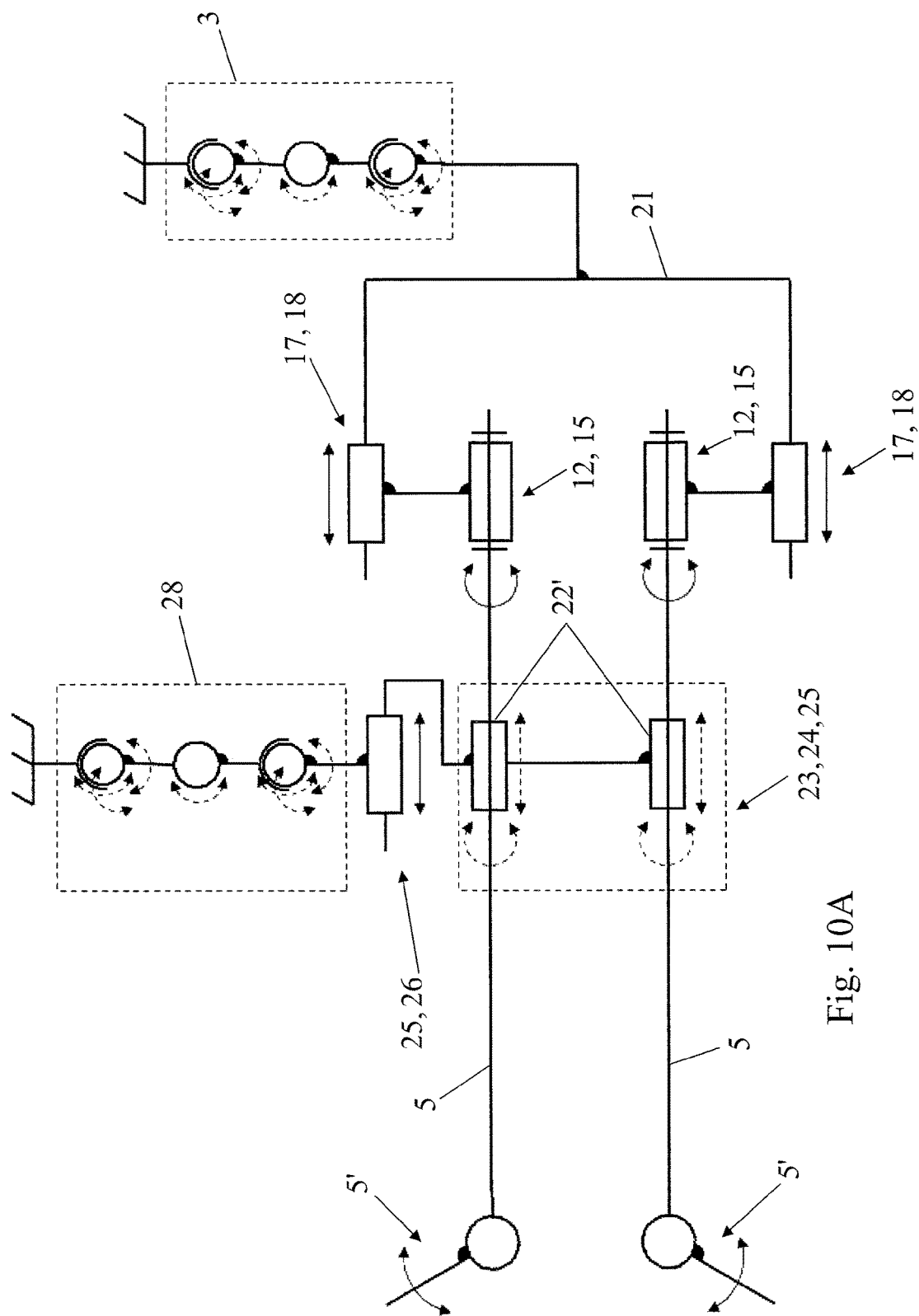
FIGS. 10A and 10B are mechanical kinematic diagrams of an endoscopic system as shown in FIGS. 1A and 1B according to two variants of a first embodiment of the invention.

By way of example, FIGS. 7 and 8 illustrate a practical embodiment of the means 7, 7', 8, 8' making possible the control of the tool 6 and the bending of the distal end portion 5' of the instrument 5 in a plane (in connection with FIGS. 9A and 9B and the kinematic diagrams of FIGS. 10A and 11A).

Thus, the actuating means 7 (FIG. 8) ensuring the actuating of the tool 6 (here, a clamp) can consist of a rotary motor transmitting its output movement by means of a helical gear, for example, to a rack mechanism whose part that moves in translation is integral with the control cable 8 connected to the clamp 6.

The actuating means 7' (FIG. 7) ensuring the bending of the end portion 5' can comprise a rotary motor that transmits its output movement by means of a helical gear and optionally a reducing gear train, for example, to a bidirectional driving part of the opposing control cables 8' that can cause the end 5' to bend.

Figure 10B:
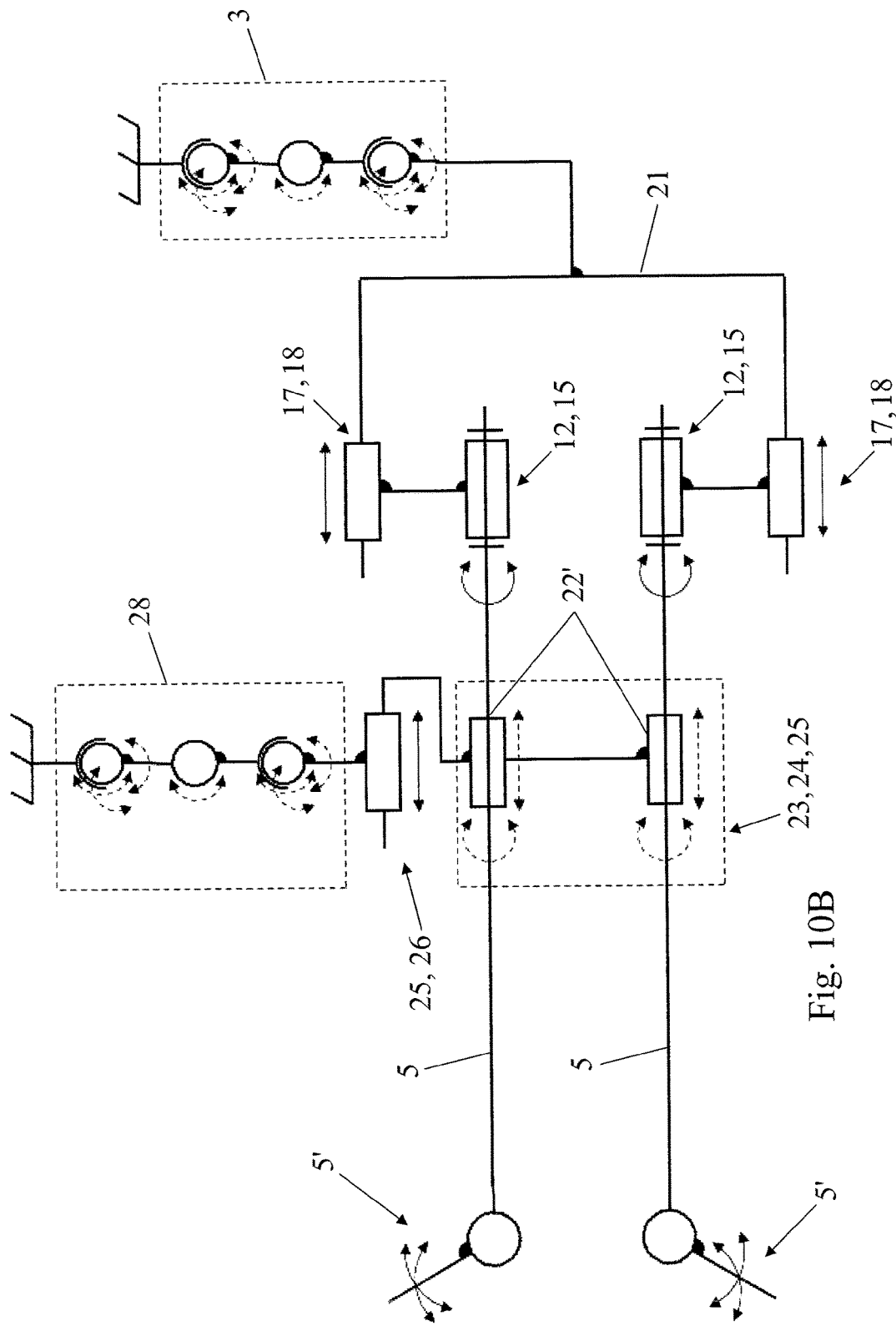

In an alternative manner, it may be provided, as emerges diagrammatically from the variants shown in FIGS. 10B and 11B, that the hollow body 10 integrates actuating means 7' and transmitting means 8' making it possible to carry out bending or arching of the distal end 5' of the medical instrument 5 in two secant planes, preferably perpendicular to one another. One skilled in the art understands that this requires only doubling the means 7' and 8' present in the hollow body 10.

Advantageously, for each instrument module 4 and optionally for each receiving housing 11, the device 1 also comprises a dedicated control unit 19 (not specifically shown) for the control of the actuating means 7, 7', and, if necessary, the motorized drive mechanism 18 and/or the motorized rotational mechanism 15, with the control unit or each control unit optionally being slaved and/or able to process measurement signals provided by one or more sensor(s) or detector(s) by means of lines 14.

The invention also relates to a flexible endoscopic system 22, as FIGS. 1A, 1B, 10A, 10B, 11A and 11B, and partially FIG. 12 show by way of examples.

This system comprises, on the one hand, an elongated body 23 with at least one, preferably at least two, longitudinal functional channel(s) 22', each intended to accommodate a medical instrument 5 whose distal end 5' carrying the actuator or the tool 6 can emerge from the distal end 23' of said elongated body 23 and, on the other hand, a control unit or control grip 24 connected to the proximal end of the elongated body 23 and comprising, for the medical instrument 5 or each medical instrument 5, an opening for introduction 24' that extends through a corresponding longitudinal channel.

This unit or grip 24 integrates actuating means controlling the bending or the arching of at least the distal end portion 23' of the elongated body 23.

This endoscopic system 22 is characterized in that it also comprises at least one motorized and modular instrumentation device 1 as described above, whose medical instrument 5 is placed in the functional channel 22' or a functional channel 22' with the ability to move in translation and in rotation.

In an advantageous, but non-limiting, manner, and as the figures of the accompanying drawings show, the instrumentation device 1 or each instrumentation device 1 comprises at least two operational units 2, whose receiving housings 11 are mounted on a crosspiece 21 or the like by means of a sliding connection 17, preferably motorized, with the relative arrangement of the operational units 2, with respect to the grip 24 or the like, held by an attachment means 27 that is stationary or integral with a plate 25 with at least one degree of freedom, being regulated in such a way that the median axes AM of the hollow bodies 10 are essentially aligned with the openings 24 for introduction of the medical instruments 5 of the grip 24 or the like.

In accordance with a possible advantageous characteristic of the endoscopic system according to the invention, and as FIGS. 1A, 1B and 12 show, the control grip 24 can be attached to a mounting plate 25, whose spatial positioning can be adjusted using an articulated support structure 28, 3.

According to a first variant embodiment, as shown in FIGS. 1A and 1B, the grip 24 is rigidly attached to the mounting plate 25 by removable attachment means 27 such as, for example, an annular attachment flange combined with a wing or a retaining pin by tightening.

So as to provide additional possibilities for movement for the endoscopic system, it may be provided that said grip 24 can be moved in translation, essentially in the direction of the longitudinal axis AL' of the flexible elongated body 23, in a controlled, preferably motorized, manner.

More specifically, and as FIG. 12 shows, the mounting plate 25 can comprise a base 25' that is made integral with the support structure 28, 3 and a trolley 25" comprising rigid and removable attachment means 27 for the grip 24, with the trolley 25" being guided in translation relative to the base 25' and moved relative to the latter owing to a motorized driving means 26, for example in the form of a motorized pinion 26' engaging either with a toothed rail or a rack that is integral with or formed on the trolley 25" or with a notched belt 26" moving said trolley 25".

The attachment means 27 used in the variant of FIG. 12 may be similar to those of FIGS. 1A and 1B.

Of course, and although not shown, it can also be considered, in a similar manner, to provide a possibility of movement in rotation relative to the axis AL' of the grip 24, optionally also of the motorized type.

Preferably, the movements of the medical instrument module(s) 4 and those of the control grip 24 are mutually slaved.

This enslavement can be mechanical in nature (mounting on the same support) or be electronic by providing a steering system that simultaneously controls the movement of the modules 4 and the grip 24.

According to a first variant embodiment as shown in FIGS. 1A, 1B, 10A and 10B, the plate 25 is carried by a support structure 28 that is separate and independent from the support structure(s) 3 carrying the instrumentation device(s) 1, for example by an articulated arm whose one end is equipped with an element 28' for the attachment or the assembly that is rigid and removable with a piece of equipment from an operating room, for example an operating table.

According to a second variant embodiment that is diagrammatically shown in FIGS. 11A and 11B, and illustrated in the form of an example of practical implementation in FIG. 13, the plate 25 or said at least one attachment means 27 is carried by the same support structure 3 as that carrying the receiving boxes 11 of the instrumentation device 1.

More specifically, and as FIG. 13 illustrates by way of practical example, it may be provided that said at least one motorized and modular instrumentation device 1 and said control unit or control grip 24 are carried by a unique support structure 3, for example in the form of an articulated arm or foot, preferably with multiple articulations. In addition, said device 1 and said grip 24 are mounted on said support structure 3 by means of a support chassis 29 providing a suitable mutual positioning configuration for the operational units 2 and the grip 24 and can be moved, in a controlled manner, in rotation and in translation relative to the support structure 3, preferably essentially around and along the longitudinal axis AL' of the elongated body 23 of the endoscopic system 22.

Two motorized degrees of freedom are thus ensured for the entire endoscopic system 22. One skilled in the art notes that this variant embodiment can be derived from that of FIGS. 1A and 1B by assimilating the support chassis 29 with a plate 25 that would also support the operational units 2.

The movements in rotation and in translation are advantageously carried out in an independent and separate manner.

Thus, the means for movement of the support chassis 29 relative to the support structure 3 comprise, on the one hand, a trolley or a pad 30 that can move in translation, in a motorized manner, relative to a plate 31 that is integral with the support structure 3, and, on the other hand, groups 32, 32' for guiding and driving in rotation the support chassis 29 attached to this trolley or pad 30.

According to a practical variant for execution of the invention, the support chassis 29 comprises, on the one hand, a superstructure 29' on which are installed, optionally by means of an articulated connection that can be locked in position, a support crosspiece 21 or the like for the operational units and the means 27 for attachment by tightening of the grip 24 or the like and, on the other hand, a substructure 29" that engages with the groups 32, 32' for guiding and driving, for example in the form of a set of curved rails 33, 33' of the substructure 29" running between roller arrangements 32, 32' or guiding or drive tensioners.

Preferably, and as FIG. 13 shows, the means for movement in rotation of the support chassis 29 can comprise two guiding tensioner groups 32 each working with a corresponding rail 33 and a group 32' of tensioners or drive pinions that engage with a toothed rail 33'.

The circular guides and drive provided by the groups 32, 32' combined with rails 33, 33' make it possible to shift these functions, thus preventing the space around the rotational/ translational axis AL' from being blocked and making it possible to install the endoscopic system there.

In the case of the variant according to FIGS. 11A and 11B and in a similar manner to the embodiment of FIG. 12, it can also be provided that the plate 25 consists of two parts that move in translation, one relative to the other, with said movement optionally being controlled and motorized (references 25, 26 in FIG. 11).

In accordance with an additional characteristic of the invention, not specifically shown, it may be provided that the flexible elongated body 23 also comprises at least one viewing channel.

In addition, a movement sensor can be combined with each actuating or drive means 7, 7', 15, 18, 26 of the operational unit 2 or each operational unit 2 and the control unit or control grip 24, with the visual signals and the signals of the sensors being transmitted to a computer unit for evaluation and control, equipped with man-machine interface means.

This computer unit can correspond to or comprise the control system that is common to the set of components of the endoscopic system.

Of course, the invention is not limited to the embodiments described and shown in the accompanying drawings. Modifications are possible, in particular from the standpoint of the composition of various elements or by substitution of equivalent techniques, without thereby exceeding the field of protection of the invention.

The invention claimed is:

1. A motorized and modular instrumentation device for an endoscope, comprising:
   at least one support structure;
   a receiving housing (11) mounted on the at least one support structure;
   at least one operational unit (2), the at least one operational unit integrating a motorized medical instrument module (4) comprising
   i) an elongated medical instrument (5) with a longitudinal axis (AL), the medical instrument configured for translational movements in a direction of the longitudinal axis (AL) of the medical instrument and to rotational movements around the longitudinal axis (AL) of the medical instrument, the medical instrument comprising an elongated body (9), a distal end portion (5'), an actuator or a tool (6) placed at a distal end of the distal end portion, the distal end portion of the medical instrument configured to undergo bending or arching in at least one plane and/or in at least one direction,
   ii) a transmission element (8, 8') extending into the elongated body (9), and
   iii) at least one motorized actuator (7, 7') controlling operation of the actuator or the tool and/or the bending or the arching of the distal end portion, where the controlling is done by the transmission element; and a hollow body (10) connected to a proximal end (5") of the medical instrument (5), the hollow body (10) having a median axis (AM) that extends the longitudinal axis (AL) of the medical instrument (5), wherein,
   the at least one motorized actuator (7, 7') is mounted in the hollow body (10), and
   said hollow body (10) is placed in the receiving housing (11), said hollow body (10) being rotatable in the receiving housing (11), via guiding elements (12), in rotation around the median axis (AM) of the hollow body (10),
   the receiving housing (11) is movably mounted on the support structure (3), at least in translation in a direction of the median axis (AM) of the hollow body (10), and
   movements of the hollow body (10) and of the receiving housing (11) are motorized, wherein,
   the hollow body (10) delimits an airtight chamber, and
   the hollow body (10) has, at least on an outside, a structure for rotation around the median axis (AM) of the hollow body (10), the hollow body (10) being cylindrical and in a form of a shell with a tapered end (10') constituting a connecting interface with the elongated body (9) of the medical instrument (5), and
   the guide elements (12) of the receiving housing (11) comprises an arrangement of at least two spaced roller bearings (12), the at least two spaced roller bearings (12) being located against the structure for rotation of the hollow body (10) to guide the hollow body (10) in rotation in the housing (11).

2. The motorized and modular instrumentation device according to claim 1,
   wherein
   the receiving housing (11) comprises a shell made in at least two parts (11', 11"), the two at least two parts (11', 11") being mutually articulated parts, one of the at least two parts (11") forming a cover that, in an open position, allows introduction and extraction of the hollow body (10), and
   said at least two parts (11', 11") of said shell comprise two opposing openings (13, 13') respectively for passage of the medical instrument (5) or a portion of an end (10') of the hollow body (10), and for passage of lines (14) for supply and/or control of the at least one motorized actuator (7, 7').

3. The motorized and modular instrumentation device according to claim 1,
   wherein said hollow body (10) includes a ring gear (16') extending peripherally around said hollow body (10), and
   wherein the receiving housing (11) comprises a motorized mechanism (15) for controlled driving, in rotation, of the hollow body (10) around the median axis (AM), the motorized mechanism (15) comprising a motorized cogwheel (16) engaged with the ring gear (16'), the connection between the hollow body (10) and the medical instrument (5) transmitting the rotation of the hollow body (10) around the median axis (AM) to the elongated body (9) of said medical instrument (5).

4. The device according to claim 1, further comprising:
   a motorized drive mechanism (18) integrated into said housing (11); and
   a connection which mounts the receiving housing (11) on the support structure (3) in the direction of the longitudinal axis (AL) of the medical instrument (5), with the movement of the receiving housing (11) relative to the support structure (3) being controlled by the motorized drive mechanism (18).

5. The device according to claim 1, wherein the support structure (3) comprises an articulated arm with a first end equipped with an element (20) for assembly with a piece of equipment from an operating room, and an opposite, second end that carries the receiving housing (11).

6. The device according to claim 1, wherein the hollow body (10) integrates the at least one motorized actuator (7') and the transmission element (8') allowing bending or arching of the distal end (5') of the medical instrument (5) in two secant planes perpendicular to one another.

7. The device according to claim 3, further comprising, for the motorized instrument module (4), a dedicated control unit (19) for control of the at least one motorized actuator (7, 7'), with the control unit being slaved to process measurement signals provided by one or more sensor(s) or detector(s).

8. Flexible endoscopic system comprising:
the motorized and modular instrumentation device (1) according to claim 1;
a further elongated body (23) with at least one longitudinal functional channel (22') that accommodates the medical instrument (5) and allows the distal end that carries the actuator or the tool (6) to emerge from a distal end of said further elongated body (23); and
a control unit or control grip (24) connected to a proximal end of the further elongated body,
the control unit or control grip (24) comprising, an introduction opening (24') that extends through a corresponding longitudinal channel for introducing the medical instrument (5),
with said control unit or control grip (24) integrating an actuator controlling bending or arching of a distal end portion (23') at least of the further elongated body,
wherein the medical instrument (5) is placed in the functional channel (22').

9. Endoscopic system according to claim 8, further comprising:
a mounting plate (25); and
an articulated support structure (28, 3),
wherein the further elongated body (23) is flexible, and
wherein the control unit or control grip (24) is attached to the mounting plate (25), a spatial positioning of the mounting plate being adjusted using the articulated support structure (28, 3), whereby said control unit or control grip (24) can be moved in translation, in a direction of a longitudinal axis (AL') of the further elongated body (23), in a controlled manner.

10. Endoscopic system according to claim 9, further comprising a motorized drive unit (26), wherein the mounting plate (25) comprises a base (25') that is made integral with the articulated support structure (28, 3) and a trolley (25") comprising a rigid and removable attachment element (27) for the control unit or control grip (24), with the trolley (25") being guided in translation relative to the base (25') and moved relative to the base (25') to a motorized drive unit (26).

11. Endoscopic system according to claim 8, wherein movements of the medical instrument module (4) and movements of the control unit or control grip (24) are mutually slaved.

12. Endoscopic system according to claim 9, wherein the articulated support structure (28) is separate and independent from the at least one support structure (3) carrying the receiving housing.

13. Endoscopic system according to claim 10, wherein the mounting plate (25) or said rigid and removable attachment element (27) is carried by the at least one same support structure (3) carrying the receiving housing (11).

14. Endoscopic system according to claim 8, wherein the motorized and modular instrumentation device (1) comprises at least two of said at least one operational unit (2), whose receiving housings (11) are mounted on a crosspiece (21) by a sliding connection (17), with a relative arrangement of the two operational units (2), relative to the control unit or control grip (24), held by an attachment element (27) in such a way that the median axes (AM) of the hollow bodies (10) are essentially aligned with the introduction opening (24') for introduction of the medical instruments (5) of the two operational units (2).

15. Endoscopic system according to claim 8, wherein said at least one motorized and modular instrumentation device (1) and said control unit or control grip (24) are carried by a unique support structure (3), in the form of an articulated arm or foot, with multiple articulations, and wherein said device (1) and said grip (24) are mounted on said support structure (3) by a support chassis (29) providing a suitable mutual positioning configuration for the operational units (2) and the grip (24) and can be moved, in a controlled manner, in rotation and in translation relative to the support structure (3), around and along the longitudinal axis (AL') of the elongated body (23) of the endoscopic system (22).

16. Endoscopic system according to claim 15, wherein the means for movement of the support chassis (29) relative to the support structure (3) comprise a trolley or a pad (30) that can move in translation, in a motorized manner, relative to a plate (31) that is integral with the support structure (3), and groups (32, 32') for guiding and driving in rotation the support chassis (29) attached to this trolley or pad (30).

17. Endoscopic system according to claim 16, wherein the support chassis (29) comprises, a superstructure (29') on which are installed, a support crosspiece (21) for the operational units (2) and an attachment element (27) for attachment by tightening of the grip (24), and, a substructure (29") that engages with the groups (32, 32') for guiding and driving, for example in the form of a set of rails (33, 33') curved from the substructure (29") running between arrangements (32, 32') of rollers or guiding or drive tensioners.

18. Endoscopic system according to claim 8, further comprising a movement sensor and a computer unit equipped with man-machine interface,
wherein the further elongated body (23) is flexible and comprises at least one viewing channel, and
wherein the movement sensor is combined with the at least one motorized actuator (7, 7'), for actuating or driving the operational unit (2) of the motorized and modular instrumentation device (1) and the control unit or control grip (24), with visual signals and signals from the movement sensor being transmitted to the computer unit for evaluation and control.

19. The device according to claim 1, wherein,
the device is for use with a flexible endoscope,
the at least one support structure is an articulated support structure,
the motorized actuator is comprised of a rotary motor and a helical gear that transmits an output movement of the rotary motor,
the receiving housing (11) comprises a shell made in at least two mutually articulated parts (11', 11"), one of the at least two parts (11") forming a cover that, in an open position, allows introduction and extraction of the hollow body (10), and
said shell comprises two opposing openings (13, 13') respectively for passage of the medical instrument (5) or a portion of an end (10') of the hollow body (10), and for passage of lines (14) for supply and/or control of the at least one motorized actuator (7, 7').

\* \* \* \* \*